United States Patent [19]

Nawata et al.

[11] Patent Number: 4,751,326

[45] Date of Patent: Jun. 14, 1988

[54] PROCESS FOR PRODUCING BENZOPHENONE-AZINE

[75] Inventors: Takanari Nawata, Kanamachi; Shuzabu Sakaguchi; Toshiaki Kohzaki, both of Ibaraki; Osamu Aoki, Chiba; Norio Takeda, Saitama; Masafumi Shimpo, Tokyo, all of Japan

[73] Assignee: Mitsubishi Gas Chemical Company, Inc., Tokyo, Japan

[21] Appl. No.: 684,419

[22] Filed: Dec. 20, 1984

Related U.S. Application Data

[63] Continuation-in-part of Ser. No. 526,312, Aug. 25, 1983, abandoned.

[30] Foreign Application Priority Data

Aug. 25, 1982 [JP] Japan ................................ 57-147151

[51] Int. Cl.$^4$ ............................................. C07C 109/04
[52] U.S. Cl. ..................................................... 564/249
[58] Field of Search ........................................ 564/249

[56] References Cited

U.S. PATENT DOCUMENTS

| | | | |
|---|---|---|---|
| 2,870,206 | 1/1959 | Meyer et al. | 564/249 |
| 4,079,080 | 3/1979 | Hayashi | 564/249 |
| 4,347,983 | 8/1982 | Isshiki et al. | 564/249 |

FOREIGN PATENT DOCUMENTS

| | | | |
|---|---|---|---|
| 71045 | 6/1978 | Japan | 564/249 |
| 137938 | 12/1978 | Japan | 564/249 |
| 28931 | 2/1980 | Japan | 564/249 |
| 55-38346 | 3/1980 | Japan | 564/249 |

OTHER PUBLICATIONS

*CRC Handbook of Chemistry and Physics*, 60th Ed. (1979–80), pp. B-75 and B-53.
*Hackh's Chemical Dictionary*, 4th Ed. (1969), McGraw-Hill Publ., p. 224.
Hiromu Hayashi et al., "Hydrazine Production from Ammonia via Azine", *Ing. Eng. Chem., Prod. Res. Dev.*, vol. 15, No. 4, 1976, pp. 299–303.
J. W. Meller, *Inorganic and Theoretical Chemistry*, vol. III, pp. 162–163.

*Primary Examiner*—James H. Reamer
*Attorney, Agent, or Firm*—Sughrue, Mion, Zinn, Macpeak & Seas

[57] ABSTRACT

An improved process for producing benzophenone-azine in which a catalyst can be removed, recovered and recycled is disclosed. The process comprises the steps of:

(a) oxidizing benzophenone-imine with molecular oxygen in the presence of cuprous chloride catalyst to produce an oxidation reaction mixture containing benzophenone-azine;

(b) contacting the oxidation reaction mixture obtained in step (a) with an aqueous solution containing ammonium chloride and hydrochloric acid to decompose the remaining benzophenone-imine substantially without causing decomposition of the produced benzophenone-azine and simultaneously to extract the catalyst from the oxidation reaction mixture;

(c) separating the oxidation reaction mixture containing benzophenone-azine after the extraction in step (b) to recover benzophenone-azine as a solution;

(d) neutralizing the catalyst-containing aqueous solution separated after the extraction step (b) with ammonia and then contacting the neutralized catalyst-containing aqueous solution with benzophenone-imine to extract the catalyst into benzophenone-imine; and (e) separating the benzophenone-imine solution containing the catalyst obtained after extraction in step (d) from the aqueous layer and recycling said solution to step (a) to reuse as a catalyst for step (a), without isolating the catalyst from said benzophenone-imine solution.

13 Claims, No Drawings

PROCESS FOR PRODUCING BENZOPHENONE-AZINE

CROSS-REFERENCE TO RELATED APPLICATIONS

This is a continuation-in-part application of U.S. application Ser. No. 526,312 filed Aug. 25, 1983 now abandoned.

FIELD OF THE INVENTION

This invention relates to a process for producing benzophenone-azine by oxidation of benzophenone-imine with molecular oxygen and, more particularly, to an improved process for producing benzophenone-azine in which a catalyst can be removed, recovered and recycled.

BACKGROUND OF THE INVENTION

Benzophenone-azine is an important intermediate for the production of hydrazine as disclosed in U.S. Pat. No. 4,239,741, and development of an economical process for the production thereof has been long desired.

Of conventional processes for producing benzophenone-azine comprising contacting benzophenone-imine with molecular oxygen in the presence of a cuprous halide, a process using cuprous chloride as a catalyst is widely known as disclosed in U.S. Pat. No. 2,870,206. In this process, it is desired that the catalyst used be recovered and reused in the production of an industrial scale.

The above-described U.S. Pat. No. 2,870,206 discloses a process wherein aqueous ammonia or an ammonium chloride aqueous solution is brought into contact with the reaction system to extract the catalyst, which is then removed from the reaction system. This U.S. patent, however, does not refer to reuse of the catalyst that would bring about an industrial advantage.

Further, Japanese Patent Application OPI (Open to Public Inspection) Nos. 71045/78 and 38346/80, etc. disclose processes in which water, aqueous ammonia or a salt solution is added to the reaction system to precipitate a copper salt, which is then recovered. However, these processes involving precipitation of a copper salt are disadvantageous in that troublesome operations inevitably associated with handling of solids, such as filtration, separation of a precipitate, transportation of a slurry, etc., are required.

SUMMARY OF THE INVENTION

As a result of extensive investigations on industrially advantageous processes for recovering and recycling the catalyst, the present inventors have completed the present invention.

The present invention relates to an improved process for producing benzophenone-azine by oxidizing benzophenoneimine with molecular oxygen in the presence of a copper halide catalyst, the improvement comprising the steps of:

(a) oxidizing benzophenone-imine with molecular oxygen in the presence of cuprous chloride catalyst while controlling the conversion of benzophenone-imine so as to maintain the molar ratio of benzophenone-imine to the cuprous chloride catalyst at 1.5 or more to produce an oxidation reaction mixture containing benzophenone-azine;

(b) contacting the oxidation reaction mixture obtained in step (a) with an aqueous solution containing ammonium chloride and hydrochloric acid to decompose the remaining benzophenone-imine substantially without causing decomposition of the produced benzophenone-azine and simultaneously to extract the catalyst from the oxidation reaction mixture, said hydrochloric acid in the aqueous solution being present in an amount of 1 to 2 times the stoichiometric amount of benzophenone-imine which remains in the oxidation reaction mixture and in an amount to provide a hydrochloric acid concentration of 1 wt% or below in the aqueous phase obtained after decomposition of benzophenone-imine;

(c) separating the oxidation reaction mixture containing benzophenone-azine after the extraction in step (b) to recover benzophenone-azine as a solution thereof;

(d) neutralizing the catalyst-containing aqueous solution separated after the extraction in step (b) with ammonia and then contacting the neutralized catalyst-containing aqueous solution with benzophenone-imine to extract the catalyst into benzophenone-imine; and (e) separating the benzophenone-imine solution containing the catalyst obtained after extraction in step (d) from the aqueous layer and recycling said solution to step (a) for reuse as a catalyst for step (a), without isolating the catalyst from the benzophenone-imine solution.

Thus, the present invention makes it possible to recover and recycle the catalyst and, consequently, to produce benzophenone-azine with industrial advantages.

DETAILED DESCRIPTION OF THE INVENTION

Benzophenone-imine used as a starting material in the process of this invention is well-known in the art. Methods for preparing benzophenone-imine include, for example, a method of reacting benzophenone with ammonia as disclosed in U.S. Pat. No. 4,083,869, a method of reacting a benzonitrile with phenyl magnesium bromide, i.e., a Grignard reagent, a method of dehydrating diphenylamino alcohol, and the like. Benzophenone-imine prepared by any of these methods can be used in the present invention.

The catalyst that can be used in the present invention is cuprous chloride.

Solvents are not particularly required in the present invention. It is preferred, however, to use solvents for the purpose of maintaining the reaction system in a solution state or facilitating oil-water separation in the extraction or back extraction. When solvents are used, solvents which are not easily oxidized in the oxidation of benzophenone-imine and, in particular, have poor affinity for water and a low viscosity are preferred. For example, benzophenone which is used as a starting material for producing benzophenone-imine and which remains in the reaction solution obtained by imination reaction of benzophenone can be suitably used as a solvent in the process of this invention. Accordingly, from the practical standpoint, it is most preferable to use an imination reaction mixture of benzophenone as it is which contains unreacted benzophenone and benzophenone-imine, as a starting material of step (a) of this invention. Reaction mixtures having a benzophenone-imine concentration of about 1 to about 90% by weight, preferably 5 to 50% by weight (the balance being unreacted benzophenone), are usually used. In case of using the imination reaction mixture as a starting material for step (a), additional solvents are not always necessary since the unreacted benzophenone remaining in the reaction mixture serves as a solvent.

Each step of the process of the present invention will now be illustrated in detail.

Step (a)

Conditions for the oxidation of benzophenone-imine are not definitely specified as varying depending on the active amount of the catalyst added to the reaction system and the like, but usually, the cuprous chloride catalyst is used in an amount ranging $1 \times 10^{-2}$ to $3 \times 10^{-1}$ mol per liter of the total volume of the reaction mixture. The reaction temperature usually ranges from 60° to 250° C., preferably from 70° to 230° C. As molecular oxygen, air, pure oxygen and other oxygen-containing gases can be used either under atmospheric pressure or under pressure. The oxygen partial pressure is preferably from 0.01 to 20 atm., more preferably from 0.05 to 10 atm., but wider ranges may also be used. The reaction may be carried out in either a batch system or a continuous system.

In step (a) of the process according to the present invention, the oxidation reaction is carried out while controlling the conversion of benzophenone-imine so as to maintain the molar ratio of benzophenone-imine to a cuprous chloride catalyst at 1.5 or more, preferably 2 or more, whereby precipitation of the catalyst in the reaction mixture can be prevented during the oxidation reaction. Since the conversion of benzophenone-imine is controlled as described above, the resulting oxidation reaction mixture obtained in step (a) contains unreacted benzophenone-imine. The conversion ratio of benzophenone-imine in the oxidation reaction generally varies depending upon the amount of the cuprous chloride catalyst used, but is generally 50 to 99.9%, preferably 80 to 99.9%.

Step (b)

In step (b), the oxidation reaction mixture obtained in step (a) is brought into contact with an aqueous solution containing ammonium chloride and a specific amount of hydrochloric acid to decompose (hydrolyze) the remaining benzophenone-imine substantially without causing any decomposition of the produced benzophenone-azine and simultaneously to extract the catalyst from the oxidation reaction mixture into the aqueous solution. In the above aqueous solution, hydrochloric acid is used in an amount of 1 to 2 times the stoichiometric amount of unreacted benzophenone-imine which remains in the oxidation reaction mixture, and also in an amount sufficient to provide a hydrochloric acid concentration of 1 wt% or below in the aqueous phase obtained after decomposition of benzophenone-imine.

Since the oxidation reaction mixture obtained in step (a) contains unreacted benzophenone-imine, when it is extracted with an aqueous solution containing only ammonium chloride, hydrolysis of benzophenone-imine is slow and insufficient; the extraction rate of the cuprous chloride catalyst is low; and the extraction efficiency is not satisfactory. However, by using an aqueous solution of ammonium chloride and a specific amount of hydrochloric acid, benzophenone-imine can be rapidly hydrolyzed to ammonium chloride and benzophenone, substantially without causing any decomposition of benzophenone-azine and the cuprous chloride catalyst can be extracted and removed with good efficiency.

The concentration of hydrochloric acid in the aqueous solution to be supplied to the extraction system cannot be definitely specified, but is usually 0.01 to 5% by weight, preferably 0.1 to 2% by weight. However, in order to avoid decomposition of benzophenone-azine, the amount of hydrochloric acid is adjusted at a hydrochloric acid concentration of 1 wt% or below in the aqueous phase obtained after decomposition of benzophenone-imine. The concentration of ammonium chloride in the aqueous solution is usually 3 to 40% by weight. The water/oil (the aqueous solution/the oxidation reaction mixture) ratio to be used in the extraction operation is not also specified, but preferably ranges from 0.05 to 20 by weight.

The amount of hydrochloric acid to be used here usually ranges from 1 to 2 equivalents, preferably 1 to 1.2 equivalents, based on the amount of benzophenone-imine fed to the extraction zone.

The extraction temperature, pressure and contact time between oil and water in step (b) are not particularly restricted, but an illustrative example is 20° to 200° C. in temperature, 0.1 to 10 atm. in pressure and 1 second to several hours in contact time.

The extraction and removal of the cuprous chloride catalyst in step (b) may be carried out either in the presence or in the absence of air. When the extraction is performed in the presence of air, the catalyst is extracted in the aqueous layer in the form of a cupric ion, which must be reduced to a cuprous ion prior to the extraction of step (d) since the extraction efficiency of the cupric ion in step (d) is low. Therefore, it is preferable that the extraction operation in step (b) is performed in the absence of air. Means for maintaining an air-free extraction system include displacement of the system with gases, such as nitrogen, helium, argon, hydrogen, methane, ethane, carbon dioxide, etc., or steam, and sealing the reaction system.

Step (c)

In step (c), the oxidation reaction mixture containing benzophenone-azine obtained after the extraction in step (b) is separated to recover benzophenone-azine as a solution thereof.

Benzophenone-azine can be recovered as crystals by removing the solvent from the solution in a conventional manner, but generally a solution of benzophenone-azine is used as a starting material for the production of hydrazine.

Step (d)

In step (d), the catalyst-containing aqueous solution separated after the extraction in step (b) is neutralized with ammonia and then contacted with benzophenone-imine to extract the catalyst from the aqueous solution.

In this step, the cuprous chloride catalyst contained in the aqueous solution obtained in step (b) is removed therefrom and transferred into the benzophenone-imine layer. The catalyst-containing benzophenone-imine solution obtained in this step is separated in step (e) and the solution per se is recycled to step (a).

In this step, it is necessary that the catalyst-containing aqueous solution is neutralized with ammonia prior to extraction with benzophenone-imine since the catalyst-containing aqueous solution contains a free acid which decomposes benzophenone-imine used as an extracting solvent.

The conditions for this catalyst extraction vary depending on the concentrations of the cuprous chloride catalyst in the aqueous solution to be extracted after neutralization with ammonia, the presence or absence of organic solvents, the method of extraction, and the like and cannot, therefore, be definitely specified. Usually, the extraction temperature ranges from 20° to 200° C., preferably 30° to 150° C., and the extraction time is in the range of from 1 second to 1 hour. The operational atmosphere is not particularly restricted, but a cuprous ion is extracted at a higher efficiency than a cupric ion as described above. Therefore, the extraction is preferably carried out in the absence of air as described with respect to the extraction in step (b).

The presence of a cupric ion in the aqueous solution to be subjected to extraction causes no inconvenience, but for the purpose of improving extraction efficiency, it is preferable to reduce the cupric ion to a cuprous ion by any means such as reacting with a reducing agent. The reducing agent which can be used for this purpose includes hydrazine, hydrazine salts, hydroxylamine salts, metal copper, sulfurous acid, sulfites, dithionous acids, phosphine, hydrophosphites, etc. It is, of course, possible to perform the reduction operation simultaneously with the extraction operation.

The amount of benzophenone-imine to be used as an extracting solvent in this step may be the whole or a part of benzophenone-imine which is subject to the oxidation reaction for producing benzophenone-azine in step (a). In the latter case, a fresh portion of benzophenone-imine is added to the extract obtained in step (e) to adjust a concentration of the cuprous chloride catalyst to the catalyst concentration required for step (a) and then recycled to the oxidation reaction in step (a).

Step (e)

In this step, the benzophenone-imine solution containing the catalyst obtained after extraction in step (d) is separated from the aqueous layer and recycled to step (a) to reuse as a catalyst for step (a), without isolating the catalyst from the benzophenone-imine solution.

More specifically, after neutralization in step (d), the cuprous chloride thus recovered in an oily layer of benzophenone-imine is reused in the form of a solution as a catalyst for the oxidation of benzophenone-imine with molecular oxygen in step (a) without any additional treatment.

As described above, the present invention makes it possible to recover and reuse the cuprous chloride catalyst by a plurality of liquid-liquid extraction steps which can be easily performed, without requiring any extra treatment, i.e., without isolating the catalyst from the recovered solution, by extracting and removing the catalyst from the reaction mixture and back extracting the catalyst from the catalyst-containing aqueous solution in the absence of air; and to easily reuse the catalyst recovered even by the extraction in the presence of air by an additional operation of reduction. Thus, the present invention provides a process for producing benzophenone-azine with great industrial advantages.

The present invention will now be illustrated in detail with reference to examples but is not deemed to be limited thereto. In these examples, Example 1 shows a process of recycling the catalyst according to steps (a) to (e) of the present invention; Example 2 and Comparative Example 1 show the effect of oxidation wherein the molar ratio of benzophenone-imine to cuprous chloride is maintained at 1.5:1 or more in step (a) of the present invention.

EXAMPLE 1

(1) Production of Benzophenone-Azine by Oxidation of Benzophenone-Imine

To 125 g of benzophenone-imine (0.691 mol) and 375 g of benzophenone was added 1.95 g (19.7 mmol) of a cuprous chloride catalyst, and the resulting mixture was stirred at 140° C. under atmospheric pressure for 2 hours while blowing oxygen gas thereinto at a rate of 1.0N l/min. The molar ratio of benzophenone-imine/cuprous chloride after completion of the oxidation reaction was 4.2. The resulting reaction mixture was found to contain benzophenone-imine and benzophenone-azine at concentrations of 3.0% and 21.5%, respectively.

(2) Extraction of Catalyst from Oxidation Reaction Mixture of Benzophenone-Imine 100 g of the reaction mixture obtained in (1) above and 50 g of each of the indicated aqueous solutions were brought into contact with each other at 90° C. for 15 minutes in a nitrogen stream while stirring to extract the cuprous chloride catalyst. The results obtained are shown in Table 1.

TABLE 1

| Run No. | Type of Aqueous Solution | Amount of Cuprous Chloride in Aqueous Layer After Extraction | HCl Concentration in Aqueous Phase After Extraction |
|---|---|---|---|
| a (Comparative) | 30% NH$_4$Cl | 3.5 mmol | |
| b (Example) | 2% HCL 10% NH$_4$Cl | 3.8 mmol | 0.79 wt % |

(3) Extraction of Catalyst with Benzophenone-Imine from Catalyst-Containing Aqueous Solution To the whole amount of the cuprous chloride-containing aqueous solution obtained in (2)-b was added 10% aqueous ammonia to adjust to a pH of 4. The resulting aqueous solution and 25 g of a benzophenone-imine solution having the same composition as that used in (1) above were brought into contact with each other at 60° C. for 3 minutes in a nitrogen stream while stirring to effect back extraction of the cuprous chloride catalyst. The amount of cuprous chloride extracted with benzophenone-imine and the percent proportion of benzophenone-imine decomposed during the extraction operation are shown in Table 2 below. For comparison, the results obtained by extraction without neutralization with aqueous ammonia are also shown in Table 2.

TABLE 2

| Run No. | Type of Aqueous Solution | Neutralization | Amount of Cuprous Chloride Extracted in Organic Layer | Percent Decomposition of Benzophenone-imine used for Extraction |
|---|---|---|---|---|
| Example | Aqueous solution | neutralized | 3.6 mmol | 8% |

TABLE 2-continued

| Run No. | Type of Aqueous Solution | Neutralization | Amount of Cuprous Chloride Extracted in Organic Layer | Percent Decomposition of Benzophenone-imine used for Extraction |
|---|---|---|---|---|
| Comparative Example | obtained in (2)-b Aqueous solution obtained in (2)-b | not neutralized | 3.3 mmol | 40% |

(4) Production of Benzophenone-Azine Using Extract of Catalyst with Benzophenone-Imine An oxidation reaction was carried out in accordance with (1) above using each of the cuprous chloride catalysts obtained by back extraction of (3). That is, the catalyst-containing benzophenone-imine solution was adjusted so that 12.5 g of benzophenone-imine (69.1 mmol) and 37.5 g of benzophenone contains 0.195 g (1.97 mmol) of cuprous chloride catalyst, and oxygen gas was introduced therein at a rate of 0.1N l/min at 140° C. under atmospheric pressure for 2 hours while stirring. The results obtained are shown in Table 3.

TABLE 3

| Composition of Reaction Mixture | |
|---|---|
| Imine | Azine |
| 3.1% | 21.4% |

EXAMPLE 2

A starting mixture was prepared by dissolving cuprous chloride containing 2,500 ppm of Cu in a solution adjusted to have a benzophenone-imine content of 23.4% with the remainder being benzophenone. 170 g of the thus prepared starting mixture was charged in 300 ml-volume glass autoclave equipped with a thermocouple sheath tube, a ring sparger for blowing gases, an opening for withdrawing gases, an opening for feeding an imine solution, an overflow tube for the reaction mixture, a manometer and an electromagnetic stirrer.

The solution was heated by external electric heat so as to maintain at 120° C. Air was introduced therein at a rate of 0.27 liter/min (volume under atmospheric pressure, hereinafter referred to as NTP) under stirring while maintaining the pressure of the system at 4 atm to effect a batchwise reaction for 1.5 hours.

After completion of the batchwise reaction, feeding of the starting material was initiated by the use of a plunger pump at a rate of 85 g/hr. Subsequently, the reaction was continuously performed for consecutive 72 hours under the same conditions as above with the feeding rate of air being 0.27 liter/min (NTP).

The waste gas containing steam after the reaction was withdrawn from the opening provided at the upper flange of the reaction vessel and led to a condenser, in which the benzophenone carried with the waste gas was condensed, released to atmospheric pressure, and allowed to escape into the atmosphere.

The reaction mixture was continuously withdrawn using a pump at a rate of 85 g/hr. The reaction mixture thus withdrawn was found to contain no precipitation of cupric chloride.

The average retention time of the reaction mixture was 2 hours, and the average conversion of benzophenone-imine was 93.1% and the selectivity to benzophenone-azine was 99%. The molar ratio of benzophenone-imine to Cu in the reaction mixture (benzophenone-imine/Cu) was 2.0. Further, the average water content in the off-gas was 6.9%.

COMPARATIVE EXAMPLE 1

The same procedure as in Example 2 was repeated except that the starting mixture has a Cu concentration of 4,000 ppm; the rate of feeding of the starting mixture and withdrawing of the reaction mixture was 74 g/hr; and the average retention time was 2.5 hours; the ratio of feeding of air under atmospheric pressure was 0.3N l/min; the average conversion of benzophenone-imine was 95.5%; and the molar ratio of benzophenone-imine to Cu in the reaction mixture (benzophenone-imine/Cu) was 0.92. After 24 hours' continuous reacting, the resulting reaction mixture was greenish black, and about 70% of the cuprous chloride used was precipitated.

While the invention has been described in detail and with reference to specific embodiments thereof, it will be apparent to one skilled in the art that various changes and modifications can be made therein without departing from the spirit and scope thereof.

What is claimed is:

1. A continuous process for producing benzophenone-azine by oxidizing benzophenone-imine with molecular oxygen in the presence of a copper halide catalyst, comprising the steps of:

(a) oxidizing benzophenone-imine in a continuous system with molecular oxygen in the presence of a cuprous chloride catalyst while controlling the conversion of benzophenone-imine so as to maintain the molar ratio of benzophenone-imine to the cuprous chloride catalyst at 1.5 or more to produce an oxidation reaction mixture containing benzophenone-azine wherein said cuprous chloride catalyst is present in a concentration of $1 \times 10^{-2}$ to $3 \times 10^{-1}$ mol per mol liter of the total volume of the reaction mixture;

(b) contacting the oxidation reaction mixture obtained in step (a) with an aqueous solution containing 3 to 40 wt% ammonium chloride and 0.01 to 5 wt% hydrochloric acid, based on the weight of the aqueous solution, in the absence of air to decompose the remaining benzophenone-imine substantially without causing decomposition of the produced benzophenone-azine and simultaneously to extract the catalyst from the oxidation reaction mixture, said hydrochloric acid in the aqueous solution being present in an amount of 1 to 2 times the stoichiometric amount of benzophenone-imine which remains in the oxidation reaction mixture and in an amount to provide a hydrochloric acid concentration of 1 wt% or below in the aqueous phase obtained after decomposition of benzophenone-imine;

(c) separating the oxidation reaction mixture containing benzophenone-azine after the extraction in step (b) to recover benzophenone-azine as a solution thereof;

(d) neutralizing the catalyst-containing aqueous solution separated after the extraction in step (b) with ammonia in the absence of air and then contacting the neutralized catalyst-containing aqueous solution with benzophenone-imine in the absence of air to extract the catalyst into benzophenone-imine; and (e) separating the benzophenone-imine solution containing the catalyst obtained after extraction in step (d) from the aqueous layer and recycling said solution to step (a) for reuse as a catalyst for step (a), without isolating the catalyst from said benzophenone-imine solution.

2. A process as claimed in claim 1, wherein benzophenone is used as a solvent in step (a).

3. A process as claimed in claim 1, wherein the oxidation in step (a) is conducted at a temperature in the range of from about 60° to about 250° C.

4. A process as claimed in claim 1, wherein said molecular oxygen in step (a) is used at an oxygen partial pressure of about 0.01 to about 20 atms.

5. A process as claimed in claim 1, wherein said extraction in step (b) is carried out at a temperature of 20° to 200° C.

6. A process as claimed in claim 1, wherein said extraction in step (b) is carried out under the pressure of 0.1 to 10 atms.

7. A process as claimed in claim 1, wherein said extraction in step (d) is carried out at a temperature of 20° to 200° C.

8. A process as claimed in claim 1, wherein the molar ratio of benzophenone-imine to the cuprous chloride catalyst is maintained at 2 or more in step (a).

9. A process as claimed in claim 1, wherein in step (a) the conversion ratio of benzophenone-imine in the oxidation reaction is 50 to 99.9%.

10. A process as claimed in claim 9, wherein the conversion ratio is 80 to 99.9%.

11. A process as claimed in claim 1, wherein step (b) the aqueous solution containing ammonium chloride and hydrochloric acid contains 0.01 to 5% by weight of hydrochloric acid.

12. A process as claimed in claim 1, wherein the aqueous solution contains 0.1 to 2% by weight of hydrochloric acid.

13. A process as claimed in claim 11, wherein the ammonium chloride is contained in an amount of 3 to 40% by weight.

* * * * *